United States Patent
Tanihara et al.

(10) Patent No.: US 7,262,275 B2
(45) Date of Patent: Aug. 28, 2007

(54) POLYPEPTIDE AND PROCESS FOR PRODUCING THE SAME

(75) Inventors: Masao Tanihara, Ikoma (JP); Chikara Otsuki, Ikoma (JP); Hiroshi Mikami, Kasugai (JP); Hisao Kinoshita, Ikoma (JP)

(73) Assignee: PHG Corporation, Kyoto (JP)

( * ) Notice: Subject to any disclaimer, the term of this patent is extended or adjusted under 35 U.S.C. 154(b) by 509 days.

(21) Appl. No.: 10/372,994

(22) Filed: Feb. 26, 2003

(65) Prior Publication Data

US 2003/0162941 A1 Aug. 28, 2003

(30) Foreign Application Priority Data

Feb. 28, 2002 (JP) ............................. 2002-053299

(51) Int. Cl.
*A61K 38/17* (2006.01)
*A61K 38/00* (2006.01)
*C07K 16/00* (2006.01)

(52) U.S. Cl. .................. 530/356; 530/329; 530/331; 530/333; 530/339; 514/21; 514/844; 514/890

(58) Field of Classification Search ............... 530/356, 530/329, 331, 333, 339; 514/21, 844; 604/890
See application file for complete search history.

(56) References Cited

U.S. PATENT DOCUMENTS 5,973,112 A * 10/1999 Raines ...................... 530/331

FOREIGN PATENT DOCUMENTS

| JP | 5-158 | 1/1993 |
|---|---|---|
| JP | 5-125100 | 5/1993 |
| JP | 6-228506 | 8/1994 |
| JP | 7-97454 | 4/1995 |
| JP | 7-278312 | 10/1995 |
| JP | 8-27192 | 1/1996 |
| JP | 8-41425 | 2/1996 |
| JP | 8-53548 | 2/1996 |
| JP | 8-276003 | 10/1996 |

OTHER PUBLICATIONS

Kishimoto et al., Biopolymers, vol. 79, pp. 163-172, 2005.*
Beck et al., Proc. Nat. Acad. Sci, USA, vol. 97, No. 8, pp. 4273-4278, Apr. 11, 2000.*
E. Miller et al., "Preparation and Characterization of the Different Types of Collagen", Methods Enzymol., vol. 82, pp. 33-64, 1982.
F. R. Brown et al., Synthesis and Structural Studies of Two-Collagen Analogues: Poly (L-prolyl-L-seryl-glycyl) and Poly (L-prolyl-L-alanyl-glycol), J. Mol. Biol., vol. 63, pp. 85-99, 1972.
D.C. Gowda et al., "Synthesis and Characterization of the Human Elastin W4 Sequence", Int. J. Peptide Protein Res., vol. 46, pp. 453-463, 1995.
A. Aguzzi et al., "Prions: Health Scare and Biological Challenge", Nature Review, vol. 2, pp. 118-126, 2001.
C. L. Jenkins et al., "Insights on the conformational stability of collagen", Natural Product Reports, Feb. 2002, vol. 19, No. 1, pp. 49-59.
G. Johnson et al., "Peptoid-containing collagen mimetics with cell binding activity", Journal of Biomedical Materials Research, Sep. 2000, vol. 51, No. 4, pp. 612-624.
J. Kwak et al., "TREN (Tris(2-aminoethyl)amine): An Effective Scaffold for the Assembly of Triple Helical Collagen Mimetic Structures", Journal of the American Chemical Society, Nov. 2002, vol. 124, No. 47, pp. 14085-14091.
M. G. Venugopal et al., "Electrostatic Interactions in Collagen-like Triple-helical Peptides", Biochemistry, Jun. 1994, vol. 33, No. 25, pp. 7948-7956.
DeTar et al., "Synthesis of Sequence Peptide Polymers Related to Collagen", *J. Org. Chem.*, vol. 37, No. 26, pp. 4377-4380, 1972.
Venkateswara et al., "Collagen Helix Stabilization by Hydroxyproline in Ala-Hyp-gly)$_n$,", *Biochemical and Biophysical Research Communications*, vol. 86, No. 3, pp. 654-660, 1979.

* cited by examiner

*Primary Examiner*—Jon Weber
*Assistant Examiner*—Abdel A Mohamed
(74) *Attorney, Agent, or Firm*—Wenderoth, Lind & Ponack, L.L.P.

(57) ABSTRACT

The invention provides for a polypeptide, which is useful as a biomaterial and free from infection. The polypeptide comprises a peptide unit of formula (1), and optionally one or more units of formulae (2) to (3): (1) $[-(OC-(CH_2)_m-CO)_p-(Pro-Y-Gly)_n-]_a$; (2) $[-(OC-(CH_2)_m-CO)_q-Z)_r-]_b$; and (3) $[-HN-R-NH-]_c$, wherein "m" is 1-18, "p" and "q" are identical or different, and each is 0 or 1, "Y" is Pro or Hyp, and "n"1-20; "Z" is a peptide chain comprising 1-10 amino acids, "r"1-20, and "R" is a linear or branched alkylene group; the molar ratio of "a" to "b"[a/b] is 100/0 to 30/70; when p=1 and q=0, c=a, when p=0 and q=1, c=b, when p=1 and q=1, c=a+b, and when p=0 and q=0, c=0; and the polypeptide shows a peak of molecular weight in a range from $1\times10^4$ to $100\times10^4$ in the molecular weight distribution.

21 Claims, 1 Drawing Sheet

POLYPEPTIDE AND PROCESS FOR PRODUCING THE SAME

This application is related to and claims priority to Japanese patent application No. 53299/2002, filed Feb. 28, 2002.

FIELD OF THE INVENTION

The present invention relates to a novel polypeptide and a process for producing the same. More specifically, the present invention relates to a novel polypeptide useful as biomaterial which is free from a risk of an infection by a pathogenic organism (or a causative factor) or an undesirable side effect, and which has a high safety, and a process for producing the same. Such a biomaterial or biocompatible material includes, for example, a medical material such as a carrier or support for a tissue engineering, a carrier or support for a regenerative medical treatment, a tissue binding agent or an antiadhesive material, a suture for a surgical operation, a hemostatic material and a contact lens; a raw material for a pharmaceutical preparation; a raw material for a cosmetic preparation; and others.

BACKGROUND OF THE INVENTION

A collagen is a fibrous protein found in all multicellular organisms. The collagen is a main component of skins or bones, and occupies 25% of total proteins in mammals. A typical collagen molecular has a rope-like superhelical structure, which is referred to as a triple helical structure, comprising three collagen polypeptide chains. The collagen is particularly rich in proline (Pro) and glycine (Gly). These two amino acid residues are important to form a stable triple helical structure of the collagen.

As methods for using a collagen as a biomaterial, there may be mentioned, for example, a method of grafting or transplanting an intact or lyophilized skin tissue derived from a pig on a skin area damaged by a burn or scald, a method of removing cellular components from a tissue with enzyme treatment, and a method of using a collagen which is solubilized by a treatment with an acidic solution or an enzyme to reconstitute a desirable form. A common preparation method and a common qualitative method are described in Methods Enzymol., Vol. 82, pp. 33 to 64, 1982.

There are various suggestions to utilize a collagen. For example, Japanese Patent Application Laid-Open No. 08-027192 (JP-08-027192A) discloses a production process of a collagen derivative for imparting moisture and smoothness to skin, which comprises esterifying and modifying an animal tissue containing a collagen with alcohol, and extracting the modified collagen, as well as a cosmetic base material using the collagen derivative.

Japanese Patent Application Laid-Open No. 07-097454 (JP-07-097454A) discloses a production process of a water-soluble crosslinked collagen which shows a high regeneration rate of a triple helical structure after thermal denaturation, and the process comprises subjecting a water-soluble collagen to a crosslinking treatment with a bifunctional alkylene diimidate cross-linker having imide ester groups at both ends of the methylene chain.

Japanese Patent Application Laid-Open No. 08-053548 (JP-08-053548A) discloses a matrix of a collagen and a synthetic polymer (a collagen-synthetic polymer matrix) which has a low immunogenicity and is useful for preparation of biocompatible implants utilized for various medical applications, and a production process of the matrix comprises reacting a collagen with a first synthetic hydrophilic polymer to form a collagen-synthetic polymer matrix, and further reacting the collagen-synthetic polymer matrix with a reactant such as a second synthetic hydrophilic polymer, a biologically active substance, a glycosaminoglycan and a derivative thereof, a chemical crosslinking agent, an esterifying agent, an amidating agent, an acylating agent, an amino acid, a polypeptide, or others.

Japanese Patent Application Laid-Open No. 07-278312 (JP-07-278312A) discloses a unit material containing a hydrophilic synthetic polymer covalently bonded to a chemically modified collagen which is substantially a non-fiberous form at pH 7. The literature discloses that the unit material is particularly useful for ophthalmological devices and optically transparent, and that the unit material has a biocompatibility.

Japanese Patent Application Laid-Open No. 05-000158 (JP-05-000158A) discloses a production process of a collagenic membrane-like substance, which comprises crushing a collagen matrix, centrifuging the crushed matrix under a high centrifugal field, homogenizing the resultant precipitate to obtain a paste, casting the paste, and drying the cast paste at a temperature of not higher than 37° C. The literature also discloses that the collagen membrane-like substance has a biocompatibility and a non-inflammatory property, and is useful for repairing a tissue as an artificial implantation matter.

Japanese Patent Application Laid-Open No. 05-125100 (JP-05-125100A) discloses a soluble fish scale collagen having high-purity and a production process thereof, and the process comprises pepsinating an intact or deashed fish scale to a pepsin treatment.

Japanese Patent Application Laid-Open No. 06-228506 (JP-06-228506A) discloses a production process of a dry particulate or powdery soluble collagen, which comprises injecting a collagen solution through a nozzle into 70 to 90% ethanol medium to form a strand-like or membranous product, drying the product, and chopping or grinding the dried product.

Japanese Patent Application Laid-Open No. 08-276003 (JP-08-276003A) discloses use of an unbaked single-crystal hydroxyapatite as a material for repairing a biological hard tissue (such as a bone), through attaching the single crystal to at least part of a low antigenic collagen fiber.

Japanese Patent Application Laid-Open No. 08-041425 (JP-08-041425A) discloses a method which comprises removing fragments of cells or tissues in a collagen solution and subjecting the residue to an alkali treatment, for removing prion in a collagen derived from an animal or human being, and discloses a collagen obtained by this method.

Moreover, regarding methods for chemical synthesis of collagen analogues, it has been reported that a soluble polyamide having a molecular weight of 16,000 to 21,000 is obtained by dissolving p-nitrophenyl ester of Pro-Ser-Gly or p-nitrophenyl ester of Pro-Ala-Gly in dimethylformamide, and adding triethylamine thereto, and allowing to stand the mixture for 24 hours (J. Mol. Biol., Vol. 63, pp. 85 to 99, 1972). In this literature, the soluble polyamide is estimated to form a triple helical structure based on the circular dichroism spectra. However there are not referred to properties of the obtained polymer.

It also has been reported that a method for obtaining a polyamide, which comprises dissolving a 50-mer peptide containing the sequence Val-Pro-Gly-Val-Gly derived from elastin in dimethylsulfoxide, adding 2 equivalents of 1-ethyl-3-(3-dimethylaminopropyl)-carbodiimide, 1 equivalent of 1-hydroxybenzotriazole and 1.6 equivalents of N-methylmorpholine thereto, allowing to stand the mixture for 14 days, and dialyzing the resultant mixture with a dialysis membrane (molecular weight cut-off: 50,000) (Int. J. Peptide Protein Res., Vol. 46, pp. 453 to 463, 1995).

Meanwhile, as described in the above-mentioned Japanese Patent Application Laid-Open No. 08-041425 (JP-08-041425A), a causative substance of sheep tremor or bovine spongiform encephalopathy is an infectious protein called as prion, and the infectious protein is considered as one of causes of human Creutzfeldt-Jakob disease infection. Prion is a protein, and it is indicated that prion is hard to deactivate with a conventional pasteurization or sterilization method, further that prion is infectious over species (Nature Review, Vol. 2, pp. 118 to 126, 2001).

In general, a collagen derived from bovine or pig is frequently used as a raw material for medical kits (devices) or pharmaceutical preparations, and cosmetic preparations. Accordingly, there have been always existed the risk of an infection (or a transmission) to pathogenic organisms or a causative factor such as prion which cannot be removed by a conventional pasteurization or sterilization.

Moreover, since various cell adhesion sites are found in a naturally occurring collagen, the naturally occurring collagen cannot exert cell selectivity for any applications. For example, in the case using a collagen as a material for inducing a nerval axon, migration or growth rate of surrounding fibroblast is more than elongation rate of the axon resulting in forming scarring tissue, and the axon cannot be elongated. It is therefore necessary to take a step to cover around the collagen with a material for protecting migration of fibroblast, or others.

SUMMARY OF THE INVENTION

It is, therefore, an object of the present invention to provide a novel polypeptide which is free from a risk of an infection (or a transmission) by a pathogenic organism (or a causative factor) or an undesirable side effect, and a process for producing the same.

It is another object of the present invention to provide a novel polypeptide useful as a highly safe biomaterial or biocompatible material, and a process for producing the same.

It is further object of the present invention to provide a process for efficiently producing a polypeptide having above-mentioned properties with inhibiting dimerization or cyclization reaction.

The inventors of the present invention made intensive studies to achieve the above objects and finally found that a collagen-like polypeptide can be produced without cyclization by condensation of a specific peptide component. The present invention was accomplished based on the above findings.

That is, the novel polypeptide of the present invention comprises peptide units represented by the following formulae (1) to (3):

  (1)

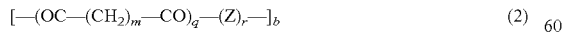  (2)

  (3)

wherein "m" denotes an integer of 1 to 18, "p" and "q" are the same or different, each representing 0 or 1, "Y" represents Pro or Hyp, and "n" denotes an integer of 1 to 20; "Z" represents a peptide chain comprising 1 to 10 amino acid residue(s), "r" denotes an integer of 1 to 20, and "R" represents a linear or blanched alkylene group; the molar ratio of "a" relative to "b" [a/b] is 100/0 to 30/70;

when p=1 and q=0, c=a,
when p=0 and q=1, c=b,
when p=1 and q=1, c=a+b, and
when p=0 and q=0, c=0.

In the polypeptide comprising the units represented by the above formulae (1) to (3), usually, "m" denotes an integer of 2 to 12; "n" denotes an integer of 2 to 15; "Z" is a peptide chain comprising at least an amino acid residue or a peptide residue selected from the group consisting of Gly, Sar, Ser, Glu, Asp, Lys, His, Ala, Val, Leu, Arg, Pro, Tyr, and Ile. Moreover, in the above formula, usually, "r" denotes an integer of 1 to 10; and "R" represents a $C_{2-12}$ alkylene group.

For example, the polypeptide of the present invention may comprise the following repeating unit (i), (ii) or (iii):

(i) a repeating unit comprising the peptide unit [-(Pro—Y—Gly)$_n$-]$_a$ (wherein "Y" and "n" have the same meanings as defined above) and the peptide unit [-(Z)$_r$-]$_b$ (wherein "Z" and "r" have the same meanings as defined above) in a ratio "a/b" of 100/0 to 40/60 (molar ratio); or (ii) a repeating unit comprising the peptide unit [—(OC—(CH$_2$)$_m$—CO)—(Pro—Y—Gly)$_n$—]$_a$ (wherein "m", "n" and "Y" have the same meanings as defined above) and the unit [—HN—R—NH—]$_c$ (wherein "R" has the same meaning as defined above) in a ratio "a/c" of substantial 1/1 (molar ratio); or (iii) a repeating unit comprising the peptide unit [—(OC—(CH$_2$)$_m$—CO)—(Pro—Y—Gly)$_n$—]a (wherein "m", "n" and "Y" have the same meanings as defined above), the peptide unit [—(OC—(CH$_2$)$_m$—CO)—(Z)$_r$—]$_b$ (wherein "m", "r" and "Z" have the same meanings as defined above) and the unit [—HN—R—NH—]$_c$ (wherein "R" has the same meaning as defined above) in a ratio "a/b" of 100/0 to 40/60 (molar ratio) and in a ratio "(a+b)/c" of substantial 1/1 (molar ratio).

The polypeptide of the present invention usually shows positive Cotton effect at a wavelength in range of 220 to 230 nm and negative Cotton effect at a wavelength in range of 195 to 205 nm in a circular dichroism spectrum. At least part (part or all) of the polypeptide, therefore, forms a triple helical structure. Moreover, the polypeptide of the present invention is capable of forming a collagenous tissue (collagen tissue or collagen-like tissue). The polypeptide of the present invention may show a peak corresponding to the molecular weight in a range from $5 \times 10^3$ to $100 \times 10^4$.

According to the present invention, the polypeptide may be produced by reacting a peptide component (A) represented by the following formula (1a) with a peptide component (B) represented by the following formula (2a):

  (1a)

wherein "X" represents H or the group HOOC—(CH$_2$)$_m$—CO— ("m" denotes an integer of 1 to 18), "Y" represents Pro or Hyp, and "n" denotes an integer of 1 to 20,

  (2a)

wherein "X" represents H or the group HOOC—(CH$_2$)$_m$—CO— ("m" denotes an integer of 1 to 18), "Z" represents a peptide chain comprising 1 to 10 amino acid residue(s), and "r" denotes an integer of 1 to 20.

In the reaction, in the case where "X" represents H in the formula (1a) and/or (2a), the reaction is conducted without the compound (C) represented by the following formula (3a). In the case where "X" represents the group HOOC—(CH$_2$)$_m$—CO— ("m" has the same meaning as defined above) in the formula (1a) and/or (2a), the reaction is conducted with the compound (C) represented by the following formula (3a):

$$H_2N-R-NH_2 \quad (3a)$$

wherein "R" represents a linear or branched alkylene group.

The ratio of the peptide component (A) relative to the peptide component (B) [the former (A)/the latter (B)] is, for example, about 100/0 to 30/70 (mol %), and the amount of the compound (C) is, for example, substantially 1 mol relative to 1 mol of the total molar amount of the peptide component (A) and/or the peptide component (B).

The reaction may be usually carried out by condensing each component (1) to (3) in a solvent (water and/or an organic solvent) in the presence of at least a dehydrating and condensing agent (e.g., a carbodiimide-series condensing agent, a fluorophosphate-series condensing agent, and a diphenylphosphorylazide). Moreover, the reaction may be carried out in the presence of the dehydrating and condensing agent and a condensing auxiliary (or a dehydrating auxiliary) [for example, an N-hydroxypolycarboxylic imide, an N-hydroxytriazole (e.g., an N-hydroxybenzotriazole such as 1-hydroxybenzotriazole), a triazine, ethyl ester of 2-hydroxyimino-2-cyanoacetic acid]. In the case where the reaction is conducted in a water-free solvent system, the proportion of the dehydrating and condensing agent may be about 0.7 to 5 mol relative to 1 mol of the total molar amount of the reaction components (1a), (2a) and (3a). In the case where the reaction is conducted in a water-containing solvent system, the proportion of the dehydrating and condensing agent may be about 2 to 500 mol relative to 1 mol of the total molar amount of the reaction components (1a) (2a) and (3a). The amount of the condensing auxiliary may be about 0.5 to 5 mol relative to the total molar amount of the above reaction components (1a), (2a) and (3a).

The present invention also includes a method for applying the polypeptide to a tissue of a subject.

DETAILED DESCRIPTION OF THE INVENTION

Figure 1:
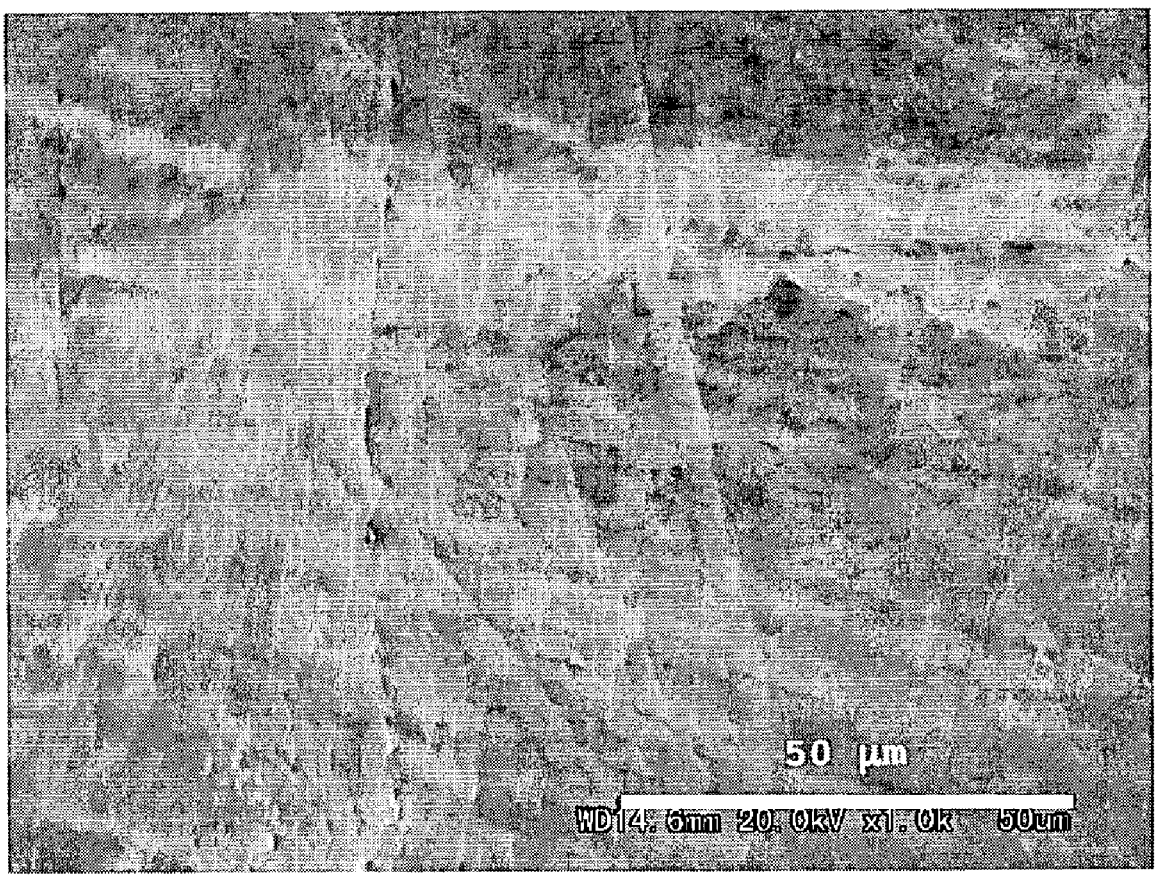
FIG. 1 is a scanning electron micrograph showing a film obtained in Example 3.

In the present invention, amino acid residues are abbreviated to the following condensation codes.
Ala: L-alanine residue
Arg: L-arginine residue
Asn: L-asparagine residue
Asp: L-aspartic acid residue
Cys: L-cysteine residue
Gln: L-glutamine residue
Glu: L-glutamic acid residue
Gly: glycin residue
His: L-histidine residue
Hyp: L-hydroxyproline residue
Ile: L-isoleucine residue
Leu: L-leucine residue
Lys: L-lysine residue
Met: L-methionine residue
Phe: L-phenylalanine residue
Pro: L-proline residue
Sar: sarcosine residue
Ser: L-serine residue
Thr: L-threonine residue
Trp: L-tryptophan residue
Tyr: L-tyrosine residue
Val: L-valine residue Moreover, in this specification, amino acid sequences of peptide chains are represented in accordance with conventional expression that, in an amino acid residue, N-terminus and C-terminus are drawn at the left and the right, respectively.

It is essential that a peptide unit (1) [—(OC—(CH$_2$)$_m$—CO)$_p$(Pro—Y—Gly)$_n$—] constituting the novel polypeptide of the present invention contains a repeating sequence Pro—Y—Gly. When the repeating number of the sequence Pro—Y—Gly is smaller, the polypeptide is deteriorated in stability of the triple helical structure. When the repeating number is too large, it is difficult to synthesize the peptide. The repeating number "n" is, therefore, about 1 to 20, preferably about 2 to 15 (e.g., about 3 to 15), and more preferably about 5 to 15.

In the above formula (1), "Y" may be either Pro or Hyp. From the viewpoint of stability of the triple helical structure, the preferred "Y" is Hyp. Incidentally, Hyp is usually 4Hyp (e.g., trans-4-hydroxy-L-proline) residue.

Further, the number "m" representing the repeating number of a methylene chain (CH$_2$) needs only to be selected from a range that the polypeptide is adversely affected physical and biological properties. The number "m" is usually about 1 to 18, preferably about 2 to 12, and more preferably about 2 to 10 (particularly about 2 to 6). The number "p" is 0 or 1.

In the above-mentioned peptide unit (2) [—(OC—(CH$_2$)—CO)—(Z)$_r$—], "Z" represents a peptide chain which has an arbitrary sequence comprising 1 to 10 amino acid residue(s). "Z" may be any sequence as far as the resulting polypeptide is not deteriorated in physical and biological properties. In order that the polypeptide shows useful physical and biological properties, for example, the peptide chain "Z" usually comprises at least one amino acid or peptide residue selected from the group consisting of Gly, Sar, Ser, Glu, Asp, Lys, His, Ala, Val, Leu, Arg, Pro, Tyr and Ile. In particular, the peptide chain "Z" practically comprises at least one amino acid or peptide residue selected from the group consisting of Gly, Ser, Glu, Asp, Lys, Arg and Pro. The peptide chain "Z" preferably comprises the amino acid residue or the sequence such as Gly, Sar, Ser, Glu, Asp, Lys, Arg-Gly-Asp, Tyr-Ile-Gly-Ser-Arg, Ile-Lys-Val-Ala-Val, Val-Pro-Gly-Val-Gly, Asp-Gly-Glu-Ala, Gly-Ile-Ala-Gly, His-Ala-Val, Glu-Arg-Leu-Glu, Lys-Asp-Pro-Lys-Arg-Leu, or Arg-Ser-Arg-Lys.

The number "r" representing the repeating number of the peptide chain "Z" needs only to be selected from a range that the resulting polypeptide demonstrates physical and biological properties. When the repeating number "r" is too large, it is difficult to synthesize the peptide, and the physical properties of the resulting polypeptide is apt to vary. The repeating number "r" is, therefore, usually about 1 to 20, preferably about 1 to 10, and more preferably about 1 to 5.

The number "m" representing the repeating number of the methylene chain (CH$_2$) is about 1 to 18, preferably about 2 to 12, and more preferably about 2 to 10 (particularly about 2 to 6) as the same manner as in the above formula (1). The number "q" is 0 or 1.

In the formulae (1) and (2), in the case where at least one of "p" and "q" is 0, the polypeptide contains the unit [—HN—R—NH—] represented by the formula (3). In the unit represented by the formula (3), a linear or blanched alkylene group represented by "R" needs only be any group as far as the polypeptide is not deteriorated in physical and biological properties. For example, as the group "R", there may be mentioned a $C_{1-18}$alkylene group such as methylene, ethylene, propylene, trimethylene, and tetramethylene groups. The alkylene group "R" may be a linear methylene chain $(CH_2)_s$ ("s" represents an integer of 1 to 18). The group "R" is preferably a $C_{2-12}$alkylene group, more preferably a $C_{2-10}$alkylene group, in particular a $C_{2-6}$alkylene group.

The ratio ["a/b"] of the peptide unit represented by the formula (1) relative to the peptide unit represented by the formula (2) is about 100/0 to 30/70 (molar ratio), preferably about 100/0 to 40/60 (molar ratio), and more preferably about 100/0 to 50/50 (molar ratio).

Further, the ratio of the unit represented by the formula (3) may be selected depending on the value "p" of the formula (1) and the value "q" of the formula (2). When "p"=1 and "q"=0, "c"=a (=1). When "p"=0 and "q"=1, "c"=b (=1). Moreover, when "p"=1 and "q"=1, "c"=a+b (=2). When "p"=0 and "q"=0, "c"=0.

That is, the polypeptide of the present invention includes the following polypeptides:
(a) a polypeptide comprising a repeating unit of the peptide unit [—(Pro—Y—Gly)$_n$—]$_a$ ("p" is 0 in the formula (1));
(b) a polypeptide which comprises a repeating unit containing the peptide unit [—(Pro—Y—Gly)$_n$—]$_a$ ("p" is 0 in the formula (1)) and the peptide unit [—(Z)$_r$—]$_b$ ("q" is 0 in the formula (2)) in a ratio of "a/b" (mol %);
(c) a polypeptide which comprises a repeating unit containing the peptide unit [—(OC—(CH$_2$)$_m$—CO)—(Pro—Y—Gly)$_n$—]$_a$ ("p" is 1 in the formula (1)) and the unit [—HN—R—NH—]$_c$ represented by the formula (3) in a ratio of "a/c" (mol %); and
(d) a polypeptide which comprises a repeating unit containing the peptide unit [—(OC—(CH$_2$)$_m$—CO)—(Pro—Y—Gly)$_n$—]$_a$ ("p" is 1 in the formula (1)), the peptide unit [—(OC—(CH$_2$)$_m$—CO)—(Z)$_r$—]$_b$ ("q" is 1 in the formula (2)) and the unit [—HN—R—NH—]$_c$ represented by the formula (3) in a ratio of "a/b/c" (mol %).

Such a polypeptide forms a linear polypeptide without forming a ring such as a six-membered ring by cyclization, and is soluble in a solvent (a hydrophilic solvent, e.g., water, an alcohol such as ethanol and propanol, a ketone such as acetone, a cyclic ether such as dioxane and tetrahydrofuran, a sulfoxide such as dimethyl sulfoxide, or a mixed solvent thereof). For example, the polypeptide shows a peak corresponding to the molecular weight in a range from about $5 \times 10^3$ to $100 \times 10^4$, and preferably from about $1 \times 10^4$ to $10 \times 10^4$ in terms of a globular protein by means of an aqueous GPC (gel permeation chromatography).

Further, the novel polypeptide of the present invention is capable of forming (formable) a collagenous tissue (collagen tissue or collagen-like tissue). That is, the polypeptide of the present invention shows positive Cotton effect at a wavelength in range of 220 to 230 nm and negative Cotton effect at a wavelength in range of 195 to 205 nm in circular dichroism spectra. At least one part (that is, part or all) of the polypeptide of the present invention is, accordingly, capable of forming a triple helical structure, and the polypeptide of the present invention forms a collagenous (collagen-like) polypeptide. Incidentally, Cotton effect means a phenomenon caused by difference between an absorption coefficient relative to a right circularly polarized light and that relative to a left at a specific wavelength in an optical rotatory substance.

The novel polypeptide of the present invention can be obtained by subjecting the above-mentioned components (1a) to (3a) to a condensation reaction. The peptide chain of the present invention can be synthesized in accordance with a conventional peptide synthesis method. Peptides may, for example, be prepared based on a solid-phase synthesis method or a liquid-phase synthesis method, and the solid-phase synthesis method is operationally convenient [for example, see "Zoku Seikagaku Jikken Kouza 2, Tanpakushitsu no Kagaku (Supplemental Handbook of Biochemical Experiments, Chemistry of Protein) (the second volume)" edited by The Japanese Biochemical Society (issued by Tokyo Kagaku Dozin Co., Ltd., May 20, 1987), pp. 641 to 694]. For the peptide synthesis, a conventional manner may be utilized, and the manner includes, for example, a coupling method using a condensing agent, an active esterification method (e.g., a phenyl ester such as p-nitrophenyl ester (ONp) and pentafluorophenyl ester (Opfp), an N-hydroxydicarboxylic imide ester such as N-hydroxysuccinimide ester (ONSu), and 1-hydroxybenzotriazole ester (Obt)), a mixed acid anhydride method, an azide method, and others. In the preferred manner, at least a condensing agent (preferably a condensing agent as mentioned below, in particular a combination of a condensing agent as mentioned below with a condensing auxiliary as mentioned below) may be practically used.

Furthermore, in the peptide synthesis, protection of an amino group, a carboxyl group, and other functional group (e.g., a guanidino group, an imidazolyl group, a mercapto group, a hydroxyl group, an ω-carboxyl group) with a protective group, and elimination or removal of the protective group with a catalytic reduction or a strong acid treatment (e.g., anhydrous hydrogen fluoride, trifluoromethanesulfonic acid, trifluoroacetic acid) are repeatedly conducted depending on a species of amino acids or peptide fragments. For example, as a protective group for an amino group, there may be utilized benzyloxycarbonyl group (Z), p-methoxybenzyloxycarbonyl group (Z(OMe)), 9-fluorenylmethoxycarbonyl group (Fmoc), t-butoxycarbonyl group (Boc), 3-nitro-2-pyridinesulfenyl group (Npys), and the other groups. As a protective group for a carboxyl group, there may be utilized benzyloxy group (OBzl), phenacyloxy group (OPac), t-butoxy group (OBu), methoxy group (OMe), ethoxy group (OEt), and the other groups. Incidentally, an automatic synthesis apparatus may be utilized for the peptide synthesis.

More specifically, the preparation of the peptide chain of the present invention with the solid-phase synthesis method may be carried out in accordance with a conventional manner. As a solid-phase resin (or a carrier), there may be utilized a polymer insoluble to a reaction solvent, for example, a styrene-divinylbenzene copolymer (such as a chloromethylated resin, a hydroxymethyl resin, a hydroxymethylphenylacetamidemethyl resin, a 4-methylbenzhydrylamine resin).

In the solid-phase synthesis method, a peptide can be usually produced by the following steps: a step forming a peptide chain corresponding to an objective peptide, and a step comprising (iv) detaching the peptide chain from the polymer (resin) and eliminating the protective group(s) from the protected functional group(s) to obtain the objective peptide, and purifying the resulting peptide. The peptide chain-forming step comprises (i) bonding an amino acid or peptide fragment to the above polymer (resin) from C-terminal to N-terminal of the objective peptide, in which the amino acid or peptide fragment has a free α-COOH group and a functional group(s) (e.g., at least an α-amino group of the N-terminal) protected with a protective group(s), (ii) eliminating the protective group of an a-amino group forming a peptide bond among the bonded amino acid or peptide fragment, and (iii) sequentially repeating the above bonding operation and the eliminating operation to elongate the peptide chain for the formation of the object peptide. In the operation (i) for bonding the amino acid or peptide fragment, an amino acid which is corresponding to the C-terminal of the peptide chain and has a free α-COOH group, and in which at least the N-terminal is protected with a protective group (for example, a Fmoc-amino acid, a Boc-amino acid) is used. Incidentally, from the viewpoint of inhibiting a side reaction, detachment of the peptide chain from the polymer is preferably carried out concurrently with elimination of the protective group with the use of trifluoroacetic acid. Moreover, the resulting peptide may be purified by utilizing a separation and purification means (e.g., a reversed phase liquid chromatography, and a gel-permeation chromatography).

In the present invention, a polypeptide is prepared by condensing at least a peptide component (A) represented by the following formula (1a):

$$X-(Pro-Y-Gly)_n-OH \quad (1a)$$

wherein "X" represents H or $HOOC-(CH_2)_m-CO-$ ("m" has the same meaning as defined above), "Y" and "n" have the same meanings as defined above.

The polypeptide of the present invention may be prepared by co-condensing the peptide component (A) represented by the above formula (1a) with a peptide component (B) represented by the following formula (2a):

$$X-(Z)_r-OH \quad (2a)$$

wherein X represents H or $HOOC-(CH_2)_m-CO-$ ("m" has the same meaning as defined above), "Z" and "r" have the same meanings as defined above.

Incidentally, as the compound in which the above group "X" is $HOOC-(CH_2)_m-CO-$, there may be mentioned, for example, a $C_{3-20}$ aliphatic dicarboxylic acid such as malonic acid, succinic acid, glutaric acid, adipic acid, pimelic acid, suberic acid, azelaic acid and sebacic acid, or an acid anhydride thereof. These compounds may be used singly or in combination. These compounds may be also subjected to a reaction according to a conventional amide bond-forming method (for example, a reaction using a tertiary amine described later as a catalyst) or the above-mentioned peptide synthesis method to obtain the compounds represented by the above formulae (1a) and (2a).

The ratio of the peptide component (A) relative to the peptide component (B) [the former (A)/the latter (B)] is, for example, about 100/0 to 30/70 (mol %), preferably about 100/0 to 40/60 (mol %), and more preferably about 100/0 to 50/50 (mol %).

Further, in the above formulae (1a) and/or (2a), if the group "X" is $HOOC-(CH_2)_m-CO-$ ("m" has the same meaning as defined above), at least one of the peptide component (A) and the peptide component (B) is subjected to a co-condensation reaction with the compound (C) represented by the following formula (3a) for forming an amide group. If the group "X" is H, it is unnecessary to use the compound (C).

$$H_2N-R-NH_2 \quad (3a)$$

"R" has the same meaning defined above.

As the compound represented by the above formula (3a), there may be exemplified a diamine corresponding to the above formula (3), e.g., a $C_{1-18}$alkylenediamine such as ethylenediamine, trimethylenediamine, propylenediamine, tetramethylenediamine and hexamethylenediamine, a polyalkylenepolyamine such as diethylenetriamine and hexamethylenetetramine, and others. These compounds may be used singly or in combination.

The amount of the diamine compound (C), for example, may be substantially 1 mol (for example, about 0.95 to 1.05 mol) relative to 1 mol of a total molar amount of the peptide component (A) and/or the peptide component (B). Incidentally, in the case where the group "X" is $HOOC-(CH_2)_m-CO-$ ("m" has the same meaning as defined above) in either the peptide component (A) or (B), the amount of the diamine compound (C) may be substantially 1 mol (for example, about 0.95 to 1.05 mol) relative to 1 mol of the peptide component having such group.

The reaction of these components (1a), (2a) and (3a) is usually carried out in a solvent. The solvent may be capable of dissolving or suspending (partly or wholly dissolving) the peptide components and the compound, and there may be usually employed water and/or an organic solvent. As the solvent, there may be mentioned, for example, water, an amide (e.g., dimethylformamide, dimethylacetamide, hexamethylphosphoramide), a sulfoxide (e.g., dimethylsulfoxide), a nitrogen-containing cyclic compound (e.g., N-methylpyrrolidone, pyridine), a nitrile (e.g., acetonitrile), an ether (e.g., dioxane, tetrahydrofuran), an alcohol (e.g., methyl alcohol, ethyl alcohol, propyl alcohol), and a mixed solvent thereof. Among these solvents, water, dimethylformamide, or dimethylsulfoxide is practically used.

The reaction of these components (1a), (2a) and (3a) may be usually carried out in the presence of at least a dehydrating agent (a dehydrating and condensing agent). The reaction with these components in the presence of a dehydrating and condensing agent and a condensing auxiliary (synergist) produces smoothly a polypeptide with inhibiting dimerization or cyclization.

The dehydrating and condensing agent is not particularly limited as far as the agent can conduct dehydration and condensation efficiently in the above-mentioned solvent. For example, the dehydrating and condensing agent (the dehydrating agent) includes a carbodiimide-series condensing agent [e.g., diisopropylcarbodiimide (DIPC), 1-ethyl-3-(3-dimethylaminopropyl)-carbodiimide (EDC=WSCI), 1-ethyl-3-(3-dimethylaminopropyl)-carbodiimide hydrochloride (WSCI HCl), dicyclohexylcarbodiimide (DCC)], a fluorophosphate-series condensing agent [e.g., O-(7-azabenzotriazole-1-yl)-1,1,3,3-tetramethyluronium hexafluorophosphate, O-benzotriazole-1-yl-N,N,N',N'-tetramethyluronium hexafluorophosphate, benzotriazole-1-yl-oxy-tris-pyrrolidinophosphonium hexafluorophosphate, a salt of benzotriazole-1-yl-tris(dimethylamino)phosphonium-hexafluorophosphide (BOP)], diphenylphosphorylazide (DPPA), and others. The dehydrating and condensing agent (s) may be used singly, or used as a mixture in combination thereof. The dehydrating and condensing agent is preferably a carbodiimide-series condensing agent [e.g., 1-ethyl-3-(3-dimethylaminopropyl)-carbodiimide, 1-ethyl-3-(3-dimethylaminopropyl)-carbodiimide hydrochloride].

The condensing auxiliary is not particularly limited as the condensing auxiliary can facilitate the reaction of the condensing agent. For example, there may be mentioned an N-hydroxypolycarboxylic imide [e.g., an N-hydroxydicarboxylic imide such as N-hydroxysuccinic imide (HONSu) and N-hydroxy-5-norbornene-2,3-dicarboxylic imide (HONB)]; an N-hydroxytriazole [e.g., an N-hydroxybenzotriazole such as 1-hydroxybenzotriazole (HOBt)]; a triazine such as 3-hydroxy-4-oxo-3,4-dihydro-1,2,3-benzotriazine (HOObt); ethyl ester of 2-hydroxyimino-2-cyanoacetic acid; and others. The condensing auxiliary may be also used singly or in combination. The condensing auxiliary is preferably an N-hydroxydicarboxylic imide [e.g., HONSu], an N-hydroxybenzotriazole or an N-hydroxybenzotriazine [e.g., HOBt].

The dehydrating and condensing agent may be suitably used in combination with the condensing auxiliary. As a combination of the dehydrating and condensing agent with the condensing auxiliary, there may be mentioned, for example, DCC-HONSu (HOBt or HOObt), WSCI-HONSU (HOBt or HOObt), and other combinations.

The amount of the dehydrating and condensing agent is, in a water-free solvent system, usually about 0.7 to 5 mol, preferably about 0.8 to 2.5 mol, and more preferably about 0.9 to 2.3 mol (e.g., about 1 to 2 mol) relative to 1 mol of the total molar amount of the reaction components (1a), (2a) and (3a). In a water-containing solvent system, since the dehydrating and condensing agent may be deactivated by water, the amount of the dehydrating and condensing agent is usually about 2 to 500 mol (e.g., about 2 to 50 mol), preferably about 5 to 250 mol (e.g., about 5 to 25 mol), and more preferably about 10 to 125 mol (e.g., about 10 to 20 mol) relative to 1 mol of a total molar amount of the reaction components (1a), (1b) and (1c). The amount of the condensing auxiliary is, for example, about 0.5 to 5 mol, preferably about 0.7 to 2 mol, and more preferably about 0.8 to 1.5 mol relative to 1 mol of a total molar amount of the reaction components (1a), (1b) and (1c) irrespective of a kind or species of solvent.

In the condensation reaction of the present invention, the pH of the reaction system may be adjusted, or a base being inert for the reaction may be added to the system. The pH may be usually adjusted with an inorganic base [e.g., sodium hydroxide, potassium hydroxide, sodium carbonate, sodium hydrogen carbonate], an organic base, an inorganic acid [e.g., hydrochloric acid], or an organic acid. The pH of the reaction mixture is usually adjusted to approximately neutral pH (pH=about 6 to 8). As the base being inert for the reaction, there may be exemplified a tertiary amine (e.g., a trialkylamine such as trimethylamine, triethylamine and diisopropylethylamine, a heterocyclic tertiary amine such as N-methylmorpholine and pyridine), and others. The amount of the base may be usually selected within a range from one to two times as much as the total molar amount of amino groups in the peptide components and the compound.

In the present invention, both the formation of the peptide chain represented by the above formula X—(Pro—Y—Gly)$_n$—OH, and the formation of a triple helical structure in the resulting polypeptide can be usually proved by measuring circular dichroism spectra or gel-permeation chromatography for a solution of the peptide chain or the polypeptide. In particular, regarding circular dichroism spectra, it has been reported that a naturally-occurring collagen and peptide chain forming a triple helical structure distinctively shows positive Cotton effect at a wavelength in range of 220 to 230 nm and negative Cotton effect at a wavelength in range of 195 to 205 nm (J. Mol. Biol., Vol. 63 pp. 85 to 99, 1972). Moreover, in accordance with gel-permeation chromatography, since a peak corresponding to a molecular weight of a trimer forming a triple helical structure is observed away from a peak corresponding to that of a monomer, the proportion of the peptide forming the triple helical structure can be determined.

The polypeptide of the present invention is capable of forming a collagenous tissue, free from a risk of an infection of a pathogenic organism or a transmission of a causative factor (e.g., a protein converted into a pathological protein, such as abnormal prion) or an undesirable side effect, and has high safety. Moreover, the polypeptide is excellent in cytophilic property and biocompatibility. The polypeptide is, therefore, useful as a biomaterial or a biocompatible material, for example, an artificial collagen. The polypeptide of the present invention may be applied to a tissue (e.g., an epidermal tissue and a dermal tissue) of a subject. The subject includes human beings, and nonhumans (such as monkeys, sheep, bovines, horses, dogs, cats, rabbits, rats, and mice). Moreover, the polypeptide of the present invention may be used for inhibiting or preventing an infection (or a transmission) originated from (caused by) a polypeptide (e.g., an infection or a transmission of a pathogenic organism or a causative factor present in a polypeptide). Accordingly, the polypeptide of the present invention may be effectively utilized in a damaged area [for example, a diseased area or an injured area (e.g., an area damaged by a scratch and a burn or scald)] or a dissected (or an incised) area [for example, a dissected area such as a surgical cut]. For example, the polypeptide is utilized as a medical material such as a carrier for a tissue engineering, a carrier for a regenerative medical treatment (e.g., an artificial skin), a tissue binding agent or an antiadhesive material, a suture for a surgical operation, a hemostatic material and a contact lens; a raw material (or base material) for a pharmaceutical preparation; a raw material (or base material) for a cosmetic preparation; a food additive; and others.

The polypeptide of the present invention can be shaped or molded by a conventional manner depending on various applications. The form to be used of the polypeptide may be a liquid form (e.g., a solution, a suspension), a particulate form, a two-dimensional form (e.g., a film, a sheet), or a three-dimensional form. For example, a sheet or film of the polypeptide may be obtained by casting a solution or suspension of the polypeptide on a releasable substrate (support) (e.g., a sheet made from a fluorine-containing resin (polytetrafluoroethylene)) and drying the cast substrate. Moreover, a fibrous substance is obtained by extruding a solution or suspension of the polypeptide through a nozzle in a solution containing a salt of high concentration or in a solvent incapable of dissolving the polypeptide. Further, a gelatinous substance may be obtained by allowing to stand an aqueous solution or suspension of the polypeptide, or if necessary, with adding a polyvalent crosslinkable reagent (e.g., glutaraldehyde) thereto. Further, a sponge-like porous substance may be obtained by lyophilizing the resultant gelatinous substance. Furthermore, a porous substance can be also obtained by stirring the aqueous solution or suspension of the polypeptide to foam, and drying.

Further, the polypeptide of the present invention may be used as a coating agent. For example, a surface of a substrate may be coated with the polypeptide of the present invention by coating or spraying with the solution or suspension of the polypeptide and drying the coated or sprayed layer. The substrate may be a shaped article made of various materials such as a metal, a ceramic, a plastic, a natural polymer, or the like. The form of the shaped article may be a two-dimensional structure or a three-dimensional structure, e.g., a particulate form, a linear or fibrous form, a film or sheet form. Further, the polypeptide may be held or supported by impregnating, into the solution or suspension of the polypeptide, a porous substance (e.g., a particulate porous substance, a two-dimensional porous substance such as a paper made from a cellulose fiber (cellulosic paper), a nonwoven or woven fabric, a three-dimensional porous substance such as a cylindrical substance).

In the case using the polypeptide of the present invention for a medical purpose, the polypeptide is preferably sterilized or pasteurized. A sterilization or pasteurization method includes various methods, for example, pasteurization with steam such as a heated and damp steam, pasteurization with a gamma ray, pasteurization with ethylene oxide gas, sterilization with a pharmaceutical preparation, sterilization with an ultraviolet ray, and others. Among these methods, pasteurization with a gamma ray and pasteurization with ethylene oxide gas are preferred from the viewpoint of pasteurization efficiency and low (or light) adverse effects on a material to be used.

The novel polypeptide of the present invention has no fear of a risk of an infection by a pathogenic organism (or a causative factor) or an undesirable side effect, with a high safety, and a high cytophilic property. Further, the polypeptide can be produced by a simple operation such as a condensation reaction without inhibition of dimerization or cyclization.

EXAMPLES

The following examples are intended to describe this invention in further detail and should by no means be interpreted as defining the scope of the invention.

Example 1

A peptide represented by the formula H—(Pro-Pro-Gly)$_{10}$—OH (Sequence ID No. 1) (manufactured by Peptide Institute, Inc.) was dissolved in water containing 50% methyl alcohol at a concentration of 0.25 mg/mL, and a circular dichroism spectrum thereof was measured with a spectrometer (J-725, manufactured by JASCO Corp., light path: 1 mm). The result showed that positive Cotton effect was observed at a wavelength of 227 nm and negative Cotton effect at a wavelength of 197 nm were observed, and confirmed that the peptide formed a triple helical structure. Moreover, with respect to the same solution, the molecular weight was measured by gel-permeation chromatography (AKTA purifier system, manufactured by Amarsham Bioscience K.K., column: Superdex Peptide PE 7.5/300, flowrate: 0.25 mL/min., eluent: 10 mM phosphate buffer (pH 7.4) containing 150 mM NaCl). The result confirmed two peaks: one peak showing a molecular weight of about 9000 corresponding to a triple helical structure, and another peak showing a molecular weight of about 3000 corresponding to a monomer. The molecular weight was calculated with a Gel Filtration LMW Calibration Kit (manufactured by Amarsham Bioscience K.K.), human insulin (manufactured by Sigma Corporation) and glycine (manufactured by Wako Pure Chemical Industries, Ltd.) as reference materials. The proportion of the peptide forming the triple helical structure was about 50% on the basis of two peak areas. Incidentally, in the case using a solution dissolving the peptide H—(Pro-Pro-Gly)$_{10}$—OH in water at a concentration of 0.25 mg/mL, weak positive Cotton effect at a wavelength of 227 nm and negative Cotton effect at a wavelength of 198 nm were observed. However, a peak corresponding to a trimer was inappreciably found in gel-permeation chromatography, and the proportion of the peptide forming the triple helical structure was almost 0%.

Five (5) mg (0.002 mmol) of the peptide H—(Pro-Pro-Gly)$_{10}$—OH was suspended in 2 mL dimethyl sulfoxide, and the mixture was stirred at a room temperature. To the mixture were added 0.31 mg (0.0024 mmol) of diisopropylethylamine, 0.32 mg (0.0024 mmol) of 1-hydroxybenzotriazole, and 0.46 mg (0.0024 mmol) of 1-ethyl-3-(3-dimethylaminopropyl)-carbodiimide hydrochloride, and the resultant mixture was further stirred for 7 days at a room temperature.

The reaction mixture (solution) was diluted 20-fold with water, and the diluted solution was subjected to a gel-permeation chromatography (AKTA purifier system, manufactured by Amarsham Bioscience K.K., column: Superdex 200 HR10/30, flowrate: 0.5 mL/min., eluent: 10 mM phosphate buffer (pH 7.4) containing 150 mM NaCl). The result confirmed a polypeptide peak in a molecular weight range of 40000 to 200000. The molecular weight was calculated with a Gel Filtration LMW Calibration Kit and a Gel Filtration HMW Calibration Kit (manufactured by Amarsham Bioscience K.K.) as reference materials.

The resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide, and the result showed that positive Cotton effect was observed at a wavelength of 227 nm and negative Cotton effect at a wavelength of 199 nm, and confirmed that the polypeptide formed a triple helical structure.

Example 2

A peptide chain represented by the formula H—(Pro-Pro-Gly)$_5$—OH (Sequence ID No. 2) was synthesized by a solid-phase synthesis with an automatic peptide synthesis machine. That is, with the use of 0.1 mmol of a particulate resin [HMP glycine, manufactured by Applied Biosystems (US)] which comprises a styrene-divinylbenzene copolymer containing 4-(Na-9-(fluorenylmethoxycarbonyl)-glycine)-oxymethyl-phenoxy-methyl group in a proportion of 0.65 mmol/g (resin) [component molar ratio of styrene relative to divinylbenzene: 99/1], the carboxyl terminal of one amino acid was sequentially linked (or bound) to the amino terminal of the other amino acid so as to obtain the object peptide. In this link reaction, 1 mmol of Nα-9-(fluorenylmethoxycarbonyl)-L-proline [Fmoc-proline] and 1 mmol of Nα-9-(fluorenylmethoxycarbonyl)-glycine [Fmoc-glycine] (manufactured by Applied Biosystems (US)) were used as amino acids in each linking step.

The peptide resin obtained in the foregoing manner was suspended in 10 mL of dimethylformamide, and 50 mg (0.5 mmol) of succinic anhydride and 13 mg (0.1 mmol) of diisopropylethylamine were added thereto. The mixture was subjected to a reaction at a room temperature for 12 hours. Thereafter, the reaction mixture was washed with methyl alcohol and dichloromethane alternately, and dried under a reduced pressure.

The peptide resin obtained by the above-mentioned manner was subjected to a treatment with 10 mL of trifluoroacetic acid containing 5% water for 3 hours. The resulting solution was added to diethyl ether to form a precipitate, and the precipitate was further washed with diethyl ether several times to deprotect the peptide and to eliminate the peptide from the resin. The resulting crude product was purified by a PD10 column (manufactured by Amarsham Bioscience K.K.) to give a peptide. The purified peptide obtained in the foregoing manner was run through "AKTA explorer10XT" manufactured by Amarsham Bioscience K.K. [column: "Nova-Pak C18", manufactured by Millipore Corporation, 3.9 mmφ×150 mm, mobile phase: a mixed solvent of acetonitrile and water containing 0.05 vol. % of trifluoroacetic acid (concentration of acetonitrile was linearly increased from 5 to 50 vol. % for 30 minutes), flow rate: 1.0 mL/min.], and a single peak was shown at a retention time of 14.5 minutes. The molecular weight of the purified peptide was determined as 1375 based on FAB method mass spectrum (theoretical value: 1374.52).

The compound HOOC—$(CH_2)_2$—CO—$(Pro-Pro-Gly)_5$—OH obtained by the above-mentioned manner was dissolved in water or water containing 50% of methyl alcohol to prepare a solution having a concentration of 0.25 mg/mL, and a circular dichroism spectrum thereof was measured with a spectrometer (J-725, manufactured by JASCO Corp., light path: 1 mm). The results in both solutions showed that no positive Cotton effect was observed at a wavelength in range of 220 to 230 nm and only negative Cotton effect was observed at a wavelength in range of 200 to 202 nm, and confirmed that the peptide did not form a triple helical structure. Moreover, with respect to the same solution, the molecular weight was measured by gel-permeation chromatography (AKTA purifier system, manufactured by Amarsham Bioscience K.K., column: Superdex Peptide PE 7.5/300, flowrate: 0.25 mL/min., eluent: 10 mM phosphate buffer (pH 7.4) containing 150 mM NaCl). The result confirmed one peak showing a molecular weight of not more than 2000 corresponding to a monomer. The molecular weight was calculated with a Gel Filtration LMW Calibration Kit (manufactured by Amarsham Bioscience K.K.), human insulin (manufactured by Sigma Corporation) and glycine (manufactured by Wako Pure Chemical Industries, Ltd.) as reference materials. The proportion of the peptide forming the triple helical structure was 0% on the basis of the peak area.

The compound HOOC—$(CH_2)_2$—CO—$(Pro-Pro-Gly)_5$—OH (1.4 mg (0.001 mmol)) and ethylenediamine (0.06 mg (0.001 mmol)) were suspended in 0.05 mL water, and to the suspended mixture were added 0.32 mg (0.0024 mmol) of 1-hydroxybenzotriazole and 4.6 mg (0.024 mmol) of 1-ethyl-3-(3-dimethylaminopropyl)-carbodiimide hydrochloride. Then, the resulting mixture was shaken at a room temperature for 3 days.

The reaction mixture was diluted 100-fold with water, and the diluted solution was subjected to a gel-permeation chromatography (AKTA purifier system, manufactured by Amarsham Bioscience K.K., column: Superdex 200 HR 10/30, flowrate: 0.5 mL/min., eluent: 10 mM phosphate buffer (pH 7.4) containing 150 mM NaCl) to determine the molecular weight of the reaction product. The result confirmed a polypeptide peak in a molecular weight range of 30000 to 200000. The molecular weight was calculated with a Gel Filtration LMW Calibration Kit and a Gel Filtration HMW Calibration Kit (manufactured by Amarsham Bioscience K.K.) as reference materials.

The resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide, and the result showed that positive Cotton effect was observed at a wavelength of 228 nm and negative Cotton effect at a wavelength of 198 nm, and confirmed that the polypeptide formed a triple helical structure.

Example 3

A peptide represented by the formula H—$(Pro-Hyp-Gly)_{10}$—OH (Sequence ID No. 3) (manufactured by Peptide Institute, Inc.) was dissolved in water or water containing 50% of methyl alcohol to prepare a solution having a concentration of 0.25 mg/mL, and a circular dichroism spectrum thereof was measured with a spectrometer (J-725, manufactured by JASCO Corp., light path: 1 mm). In water, the result showed that positive Cotton effect was observed at a wavelength of 225 nm and negative Cotton effect at a wavelength of 195 nm, and confirmed that the peptide formed a triple helical structure. Moreover, the same solution was subjected to a gel-permeation chromatography (AKTA purifier system, manufactured by Amarsham Bioscience K.K., column: Superdex Peptide PE 7.5/300, flowrate: 0.25 mL/min., eluent: 10 mM phosphate buffer (pH 7.4) containing 150 mM NaCl) thereby confirming one peak showing a molecular weight of about 9000 corresponding to a triple helical structure. The molecular weight was calculated with a Gel Filtration LMW Calibration Kit (manufactured by Amarsham Bioscience K.K.), human insulin (manufactured by Sigma Corporation) and glycine (manufactured by Wako Pure Chemical Industries, Ltd.) as reference materials. The proportion of the peptide forming the triple helical structure was about 100% on the basis of the peak area. Also, in the case of water containing 50% of methyl alcohol, almost the same results were given, and the proportion of the peptide forming the triple helical structure was about 100%.

Five (5) mg (0.0016 mmol) of the peptide H—$(Pro-Hyp-Gly)_{10}$—OH was suspended in 2 mL dimethyl sulfoxide, and the mixture was stirred at a room temperature. To the mixture were added 0.23 mg (0.0018 mmol) of diisopropylethylamine, 0.24 mg (0.0018 mmol) of 1-hydroxybenzotriazole, and 0.65 mg (0.0034 mmol) of 1-ethyl-3-(3-dimethylaminopropyl)-carbodiimide hydrochloride, and the resultant mixture was further stirred for 7 days at a room temperature.

The reaction mixture was diluted 20-fold with water, and the diluted solution was subjected to a gel-permeation chromatography (AKTA purifier system, manufactured by Amarsham Bioscience K.K., column: Superdex 200 HR 10/30, flow rate: 0.5 mL/min., eluent: 10 mM phosphate buffer (pH 7.4) containing 150 mM NaCl). The result confirmed a polypeptide peak was observed in a molecular weight range of 60000 to not less than 200000. The molecular weight was calculated with a Gel Filtration LMW Calibration Kit and a Gel Filtration HMW Calibration Kit (manufactured by Amarsham Bioscience K.K.) as reference materials.

The resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide. The result showed that positive Cotton effect was observed at a wavelength of 225 nm and negative Cotton effect at a wavelength of 197 nm, and confirmed that the polypeptide formed a triple helical structure.

The water suspension containing the resulting polypeptide was cast on a sheet made from a fluorine-containing resin (polytetrafluoroethylene), and the cast sheet was air-dried to obtain a cast film. Gold was deposited on the film, and the deposited film was observed with the use of a scanning electron microscope. As a result, a fibrous structure was observed as shown in FIG. 1.

Example 4

A peptide represented by the formula H—$(Pro-Pro-Gly)_5$—OH (manufactured by Peptide Institute, Inc.) was dissolved in water or water containing 50% of methyl alcohol to prepare a solution having a concentration of 0.25 mg/mL, and a circular dichroism spectrum thereof was measured with a spectrometer (J-725, manufactured by JASCO Corp., light path: 1 mm). The results in both solutions showed that no positive Cotton effect was observed at a wavelength in range of 220 to 230 nm and only negative Cotton effect was observed at a wavelength in range of 200 to 202 nm, and confirmed that the peptide did not form a triple helical structure. Moreover, the same solutions were subjected to a gel-permeation chromatography (AKTA purifier system, manufactured by Amarsham Bioscience K.K., column: Superdex Peptide PE 7.5/300, flow rate: 0.25 mL/min., eluent: 10 mM phosphate buffer (pH 7.4) containing 150 mM NaCl). The result confirmed one peak showing a molecular weight of not more than 2000 corresponding to a monomer. The molecular weight was calculated with a Gel Filtration LMW Calibration Kit (manufactured by Amarsham Bioscience K.K.), human insulin (manufactured by Sigma Corporation) and glycine (manufactured by Wako Pure Chemical Industries, Ltd.) as reference materials. The proportion of the peptide forming the triple helical structure was 0% on the basis of the peak area.

The peptide H—(Pro-Pro-Gly)$_5$—OH (3.5 mg (0.0026 mmol)) and the peptide H—(Val-Pro-Gly-Val-Gly)$_2$—OH (Sequence ID No. 4) (0.92 mg (0.0011 mmol)) synthesized in the same manner as in Example 2 were suspended in 1.5 mL dimethyl sulfoxide in a predetermined proportion, and the suspension was stirred at a room temperature. To the mixture were added 0.52 mg (0.0040 mmol) of diisopropylethylamine, 0.51 mg (0.0038 mmol) of 1-hydroxybenzotriazole, and 1.45 mg (0.0076 mmol) of 1-ethyl-3-(3-dimethylaminopropyl)-carbodiimide hydrochloride, and the resultant mixture was further stirred for 7 days at a room temperature.

The reaction mixture was diluted 20-fold with water, and the diluted solution was subjected to a gel-permeation chromatography (AKTA purifier system, manufactured by Amarsham Bioscience K.K., column: Superdex 200 HR 10/30, flow rate: 0.5 mL/min., eluent: 10 mM phosphate buffer (pH 7.4) containing 150 mM NaCl) to determine the molecular weight of the resulting polypeptide. The result confirmed a polypeptide peak in a molecular weight range of 80000 to 450000. The molecular weight was calculated with a Gel Filtration LMW Calibration Kit and a Gel Filtration HMW Calibration Kit (manufactured by Amarsham Bioscience K.K.) as reference materials.

The resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide. The result showed that positive Cotton effect was observed at a wavelength of 227 nm and negative Cotton effect at a wavelength of 198 nm, and confirmed that the polypeptide formed a triple helical structure.

The water suspension containing the resulting polypeptide was cast on a sheet made of a fluorine-containing resin (polytetrafluoroethylene), and the cast sheet was air-dried to obtain a cast film. The film was immersed in 10 mM phosphate buffer (pH 7.4) containing 150 mM NaCl to give a gel sheet. The gel sheet was transparent at a room temperature, and was reversibly clouded at a temperature of not lower than 40° C.

Example 5

A peptide represented by the formula H—(Pro-Hyp-Gly)$_5$—OH (Sequence ID No. 5) (manufactured by Peptide Institute, Inc.) was dissolved in water or water containing 50% of methyl alcohol to prepare a solution having a concentration of 0.25 mg/mL, and a circular dichroism spectrum thereof was measured with a spectrometer (J-725, manufactured by JASCO Corp., light path: 1 mm). In water, the result showed that positive Cotton effect was observed at a wavelength of 223 nm and negative Cotton effect at a wavelength of 201 nm, and confirmed that the peptide formed a triple helical structure. Moreover, the same solution was subjected to a gel-permeation chromatography (AKTA purifier system, manufactured by Amarsham Bioscience K.K., column: Superdex Peptide PE 7.5/300, flow-rate: 0.25 mL/min., eluent: 10 mM phosphate buffer (pH 7.4) containing 150 mM NaCl) thereby confirming one peak showing a molecular weight of about 4100 corresponding to a triple helical structure. The molecular weight was calculated with a Gel Filtration LMW Calibration Kit (manufactured by Amarsham Bioscience K.K.), human insulin (manufactured by Sigma Corporation) and glycine (manufactured by Wako Pure Chemical Industries, Ltd.) as reference materials. The proportion of the peptide forming the triple helical structure was about 100% on the basis of the peak area. Also, in the case of water containing 50% of methyl alcohol, almost the same results were given, and the proportion of the peptide forming the triple helical structure was about 100%.

Five (5) mg (0.0033 mmol) of the peptide H—(Pro-Hyp-Gly)$_5$—OH was suspended in 2 mL dimethyl sulfoxide, and the mixture was stirred at a room temperature. To the mixture were added 0.44 mg (0.0034 mmol) of diisopropylethylamine, 0.46 mg (0.0033 mmol) of 1-hydroxybenzotriazole, and 1.3 mg (0.0068 mmol) of 1-ethyl-3-(3-dimethylaminopropyl)-carbodiimide hydrochloride, and the resultant mixture was further stirred for 14 days at a room temperature.

The reaction mixture was diluted 20-fold with water, and the diluted solution was subjected to a gel-permeation chromatography (AKTA purifier system, manufactured by Amarsham Bioscience K.K., column: Superdex 200 HR 10/30, flow rate: 0.5 mL/min., eluent: 10 mM phosphate buffer (pH 7.4) containing 150 mM NaCl). A polypeptide peak was observed in a molecular weight range of 40000 to not less than 100000. The molecular weight was calculated with a Gel Filtration LMW Calibration Kit and a Gel Filtration HMW Calibration Kit (manufactured by Amarsham Bioscience K.K.) as reference materials.

The resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide. The result showed that positive Cotton effect was observed at a wavelength of 224 nm and negative Cotton effect at a wavelength of 199 nm, and confirmed that the polypeptide formed a triple helical structure.

Example 6

Five (5) mg (0.0016 mmol) of a peptide represented by the formula: H—(Pro-Hyp-Gly)$_{10}$—OH (Sequence ID No. 3) (manufactured by Peptide Institute, Inc.) was dissolved in 0.5 mL of 10 mM phosphate buffer (containing 8.1 mM Na$_2$HPO$_4$.12H$_2$O, 1.5 mM KH$_2$PO$_4$ and 2.7 mM KCl, pH 7.4), and the solution was stirred at 20° C. To the solution were added 0.24 mg (0.0018 mmol) of 1-hydroxybenzotriazole and 31 mg (0.16 mmol) of 1-ethyl-3-(3-dimethylaminopropyl)-carbodiimide hydrochloride, and the resultant mixture was further stirred for 24 hours at 20° C.

The reaction mixture was diluted 60-fold with water, and the diluted solution was subjected to a gel-permeation chromatography (AKTA purifier system, manufactured by Amarsham Bioscience K.K., column: Superose 6 HR 10/30, flow rate: 0.5 mL/min., eluent: 10 mM phosphate buffer (pH 7.4) containing 150 mM NaCl) to determine the molecular weight of the reaction product. The result confirmed a polypeptide peak corresponding to an average molecular weight of 400000. The molecular weight was calculated with a Gel Filtration LMW Calibration Kit and a Gel Filtration HMW Calibration Kit (manufactured by Amarsham Bioscience K.K.) as reference materials.

Moreover, the resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide, and the result showed that positive Cotton effect was observed at a wavelength of 225 nm and negative Cotton effect at a wavelength of 197 nm, and confirmed that the polypeptide formed a triple helical structure.

Example 7

A peptide represented by the formula: H—(Pro-Hyp-Gly)$_1$—OH (manufactured by Peptide Institute, Inc.) was dissolved in water to prepare a solution having a concentration of 0.25 mg/mL, and a circular dichroism spectrum thereof was measured with a spectrometer (J-820, manufactured by JASCO Corp., light path: 1 mm). The results showed that positive Cotton effect was observed at a wavelength of 214 nm and negative Cotton effect at a wavelength of 196 nm, and confirmed that the peptide did not form a triple helical structure. Moreover, with respect to the same solution, the molecular weight was measured by gel-permeation chromatography (AKTA purifier system, manufactured by Amarsham Bioscience K.K., column: Superdex Peptide PE 7.5/300, flow rate: 0.25 mL/min., eluent: 10 mM phosphate buffer (pH 7.4) containing 150 mM NaCl). The result confirmed one peak showing a molecular weight of about 250 corresponding to a monomer. The molecular weight was calculated with a Gel Filtration LMW Calibration Kit (manufactured by Amarsham Bioscience K.K.), human insulin (manufactured by Sigma Corporation) and glycine (manufactured by Wako Pure Chemical Industries, Ltd.) as reference materials. The proportion of the peptide forming the triple helical structure was 0%.

Twenty-five (25) mg (0.088 mmol) of a peptide represented by the formula: H—(Pro-Hyp-Gly)$_1$—OH was dissolved in 2.5 mL of 10 mM phosphate buffer (pH 7.4), and the solution was stirred at 20° C. To the solution were added 12.1 mg (0.09 mmol) of 1-hydroxybenzotriazole and 168 mg (0.88 mmol) of 1-ethyl-3-(3-dimethylaminopropyl)-carbodiimide hydrochloride, and the resultant mixture was further stirred for 24 hours at 20° C.

The reaction mixture was diluted 20-fold with water, and the diluted solution was subjected to a gel-permeation chromatography (AKTA purifier system, manufactured by Amarsham Bioscience K.K., column: Superdex 200 HR 10/30, flow rate: 0.5 mL/min., eluent: 10 mM phosphate buffer (pH 7.4) containing 150 mM NaCl) to determine the molecular weight of the reaction product. The result confirmed a polypeptide peak in a molecular weight range of 20000 to 30000. The molecular weight was calculated with a Gel Filtration LMW Calibration Kit and a Gel Filtration HMW Calibration Kit (manufactured by Amarsham Bioscience K.K.) as reference materials.

The resulting reaction mixture was diluted 5-fold with water, and the diluted solution was dialyzed against water for 3 days to remove the reagent(s) such as the condensing agent and the unreacted monomer(s). The circular dichroism spectrum was measured in the obtained polypeptide, and the result showed that positive Cotton effect was observed at a wavelength of 225 nm and negative Cotton effect at a wavelength of 199 nm, and confirmed that the polypeptide formed a triple helical structure.

Test Example

A cast film was made from each polypeptide manufactured in Examples 1 and 3, and the film was pasteurized with 25 kGy gamma irradiation. About 10,000 of mouse normal fibroblast strain NIH3T3 were dispersed on the film, and was incubated in an Eagle's Minimum Essential Medium containing 10% bovine fetal serum in the presence of 5% $CO_2$ at 37° C. for 3 days. The NIH3T3 cell was well adhered to and proliferated on the film made from each polypeptide obtained in Examples 1 and 3, and was no abnormality in configuration or others.

---

What is claimed is:

1. A polypeptide comprising a peptide unit represented by formula (1) below and optionally one or more units represented by formulae (2) to (3) below:

$$[-(OC-(CH_2)_m-CO)_p-(Pro-Y-Gly)_n-]_a \quad (1);$$

$$[-(OC-(CH_2)_m-CO)_q-(Z)_r-]_b \quad (2); \text{ and}$$

$$[-HN-R-NH-]_c \quad (3),$$

wherein "m" denotes an integer of 1 to 18, "p" and "q" are the same or different, each representing 0 or 1, "Y" represents Pro or Hyp, and "n" denotes an integer of 1 to 20; "Z" represents a peptide chain comprising 1 to 10 amino acid residue(s), "r" denotes an integer of 1 to 20, and "R" represents a linear or branched alkylene group; the molar ratio of "a" relative to "b" [a/b] is 100/0 to 30/70;

when p=1 and q=0, c=a, when p=0 and q=1, c=b, when p=1 and q=1, c=a+b, and when p=0 and q=0, c=0; and wherein the polypeptide shows a peak of molecular weight in a range from 60 kD to 1000 kD in the molecular weight distribution in terms of globular protein by means of an aqueous gel permeation chromatography, and at least part of the polypeptide forms a triple helix.

2. The polypeptide according to claim 1, wherein "m" denotes an integer of 2 to 12; "n" denotes an integer of 2 to 15; "Z" is a peptide chain comprising at least an amino acid residue or a peptide residue selected from the group consisting of Gly, Sar, Ser, Glu, Asp, Lys, His, Ala, Val, Leu, Arg, Pro, Tyr, and Ile; "r" denotes an integer of 1 to 10; and "R" represents a $C_{2-12}$ alkylene group.

3. The polypeptide according to claim 1, which shows positive Cotton effect at a wavelength in n range of 220 to 230 nm and negative Cotton effect at a wavelength in a range of 195 to 205 nm in a circular dichroism spectrum.

4. The polypeptide according to claim 1, wherein the polypeptide shows a peak of molecular weight in a range from 60 kD to 200 kD in the molecular weight distribution in terms of globular protein by means of an aqueous gel permeation chromatography.

5. The polypeptide according to claim 1, wherein the polypeptide shows a peak of molecular weight in a range from 80 kD to 450 kD in the molecular weight distribution in terms of globular protein by means of an aqueous gel permeation chromatography.

6. A biomaterial or biocompatible material comprising the polypeptide according to claim 1.

7. A cosmetic preparation comprising the polypeptide according to claim 1.

8. A food additive comprising the polypeptide according to claim 1.

9. A composition for use in a pharmaceutical composition said, composition comprising the polypeptide according to claim 1 together with a liquid or solid substrate.

10. A medical material comprising the polypeptide according to claim 1.

11. The medical material according to claim 10, wherein the medical material is a tissue engineering carrier, a regenerative medical treating carrier, a tissue binding agent, an antiadhesive material, a surgical operating suture, a hemostatic material or a contact lens.

12. A method comprising applying the polypeptide according to claim 1 to a tissue of a subject.

13. A process for producing the polypeptide according to claim 1, which comprises reacting a peptide component (A) represented by the following formula (1a) with a peptide component (B) represented by the following formula (2a) and a compound (C) represented by the following formula (3a), as an optional component:

X-(Pro-Y-Gly)$_n$—OH     (1a)

wherein "X" represents H or the group HOOC—(CH$_2$)$_m$—CO— ("m" denotes an integer of 1 to 18), "Y" represents Pro or Hyp, and "n" denotes an integer of 1 to 20,

X-(Z)$_r$—OH     (2a)

wherein "X" represents H or the group HOOC—(CH$_2$)$_m$—CO— ("m" denotes an integer of 1 to 18), "Z" represents a peptide chain comprising 1 to 10 amino acid residue(s), and "r" denotes an integer of 1 to 20,

H$_2$N—R—NH$_2$     (3a)

wherein "R" represents a linear or branched alkylene group, wherein the ratio of the peptide component (A) relative to the peptide component (B) [the former (A)/the latter (B)] is 100/0 to 30/70 (mol %); provided that in the case where "X" represents the group HOOC—(CH$_2$)$_m$—CO— ("m" has the same meaning as defined above) in the formula (1a) and/or (2a), the amount of the compound (C) is substantially 1 mol relative to 1 mol of the total molar amount of the peptide component (A) and/or the peptide component (B); and in the case where "X"0 represents H in the formula (1a) and/or (2a), the reaction is conducted without the compound (C).

14. The process according to claim 13, wherein the reaction is carried out in the presence of at least a dehydrating and condensing agent.

15. The process according to claim 14, wherein the dehydrating and condensing agent comprises at least one member selected from the group consisting of a carbodiimide-series condensing agent, a fluorophosphate-series condensing agent, and a diphenylphosphorylazide.

16. The process according tea claim 14 which is conducted in a water-free solvent system, wherein the proportion of the dehydrating and condensing agent is 0.7 to 5 mol relative to 1 mol of the total molar amount of said reaction components (1a), (2a) and (3a).

17. The process according to claim 14 which is conducted in a water-containing solvent system, wherein the proportion of the dehydrating and condensing agent is 2 to 500 mol relative to 1 mol of the total molar amount of said reaction components (1a), (2a) and (3a).

18. The process according to claim 13, wherein the reaction is carried out in the presence of a dehydrating and condensing agent and a condensing auxiliary.

19. The process according to claim 18, wherein the condensing auxiliary comprises at least one member selected from the group consisting of an N-hydroxypolycarboxylic imide, an N-hydroxytriazole, a triazine, and ethyl ester of 2-hydroxyimino-2-cyanoacetic acid.

20. The process according to claim 18, wherein the amount of the condensing auxiliary is 0.5 to 5 mol relative to the total molar amount of said reaction components (1a), (2a) and (3a).

21. A polypeptide comprising a peptide unit represented by the following formula:

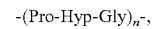

-(Pro-Hyp-Gly)$_n$-, wherein "n" denotes an integer of 1 to 15, and the polypeptide shows a peak of molecular weight in a range from 60 kD to 1000 kD in the molecular weight distribution in terms of globular protein by means of an aqueous gel permeation chromatography, and at least part of the polypeptide forms a triple helical structure.

* * * * *

UNITED STATES PATENT AND TRADEMARK OFFICE
CERTIFICATE OF CORRECTION

| | | |
|---|---|---|
| PATENT NO. | : 7,262,275 B2 | Page 1 of 1 |
| APPLICATION NO. | : 10/372994 | |
| DATED | : August 28, 2007 | |
| INVENTOR(S) | : Masao Tanihara et al. | |

It is certified that error appears in the above-identified patent and that said Letters Patent is hereby corrected as shown below:

In column 23, claim 2, line 6, please change "lie" to --lle--.

Signed and Sealed this

First Day of April, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence:peptide

<400> SEQUENCE: 1

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

```
<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence:peptide

<400> SEQUENCE: 2

Pro Pro Gly Pro Pro Gly Pro Pro Gly Pro Pro Gly Pro Pro Gly
1               5                   10                  15

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence:peptide
<220> FEATURE:
<221> NAME/KEY: misc_feature
<222> LOCATION: (1)..(30)
<223> OTHER INFORMATION: Xaa is defiend as 4Hyp

<400> SEQUENCE: 3

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:peptide

<400> SEQUENCE: 4

Val Pro Gly Val Gly Val Pro Gly Val Gly
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:peptide
<220> FEATURE:
<221> NAME/KEY: MISC_FEATURE
<222> LOCATION: (1)..(15)
<223> OTHER INFORMATION: Xaa is defined as 4Hyp

<400> SEQUENCE: 5

Pro Xaa Gly Pro Xaa Gly Pro Xaa Gly Pro Xaa Gly Pro Xaa Gly
1               5                   10                  15
```